US00PP17868P2

(12) United States Plant Patent
Kearley, Jr.

(10) Patent No.: US PP17,868 P2
(45) Date of Patent: Jul. 17, 2007

(54) ***LANTANA* PLANT NAMED 'LAX 600'**

(50) Latin Name: *Lantana camara*
Varietal Denomination: LAX 600

(75) Inventor: Richard C. Kearley, Jr., Hawthorne, FL (US)

(73) Assignee: Robrick Nursery, Inc., Hawthorne, FL (US)

( * ) Notice: Subject to any disclaimer, the term of this patent is extended or adjusted under 35 U.S.C. 154(b) by 12 days.

(21) Appl. No.: 11/267,908

(22) Filed: Nov. 4, 2005

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Lantana* plant named 'LAX 600', characterized by its compact, upright and somewhat outwardly spreading plant habit; short internodes; relatively small leaves; early, freely and continuous flowering habit; inflorescences with initially golden yellow-colored flowers that become orange and eventually light red with development; and low seed set.

1 Drawing Sheet

Botanical designation: *Lantana camara.*
Cultivar denomination: 'LAX 600'.

BACKGROUND OF THE INVENTION

The present Invention relates to a new and distinct cultivar of *Lantana* plant, botanically known as *Lantana camara,* and hereinafter referred to by the cultivar name LAX 600.

The new *Lantana* is a product of a planned breeding program conducted by the Inventor in Hawthorne, Fla. The objective of the breeding program is to create compact *Lantanas* with little to no seed set.

The new *Lantana* originated from an open pollination in September, 1999 of the *Lantana* cultivar Tangerine, not patented, as the female, or seed parent, with an unidentified *Lantana* selection as the male, or pollen parent. The new *Lantana* was selected as a single flowering plant from the resulting progeny of the open pollination by the Inventor in a controlled environment in Hawthorne, Fla. in June, 2000, on the basis of its growth habit and attractive flower coloration.

Asexual reproduction of the new cultivar by terminal cuttings in a controlled environment in Hawthorne, Fla., since July, 2000, has shown that the unique features of this new *Lantana* are stable and reproduced true to type in successive generations.

SUMMARY OF THE INVENTION

Plants of the cultivar LAX 600 have not been observed under all possible environmental conditions. The phenotype may vary somewhat with variations in environment and culture such as temperature and light intensity, without however, any variance in genotype.

The following traits have been repeatedly observed and are determined to be the unique characteristics of 'LAX 600'. These characteristics in combination distinguish 'LAX 600' as a new and distinct *Lantana* cultivar:

1. Compact, upright and somewhat outwardly spreading plant habit.
2. Short internodes.
3. Relatively small leaves.
4. Early, freely and continuous flowering habit.
5. Inflorescences with initially golden yellow-colored flowers that become orange and eventually light red with development.
6. Low seed set.

Plants of the new *Lantana* can be compared to plants of the female parent, the cultivar Tangerine. In side-by-side comparisons conducted in Hawthorne, Fla., plants of the new *Lantana* differed from plants of the cultivar Tangerine in the following characteristics:

1. Plants of the new *Lantana* were more compact than plants of the cultivar Tangerine.
2. Plants of the new *Lantana* had shorter internodes than plants of the cultivar Tangerine.
3. Plants of the new *Lantana* were more freely flowering than plants of the cultivar Tangerine.
4. Plants of the new *Lantana* had golden yellow, orange and light red-colored flowers whereas plants of the cultivar Tangerine had orange-colored flowers.
5. Plants of the new *Lantana* produced fewer seeds than plants of the cultivar Tangerine.

Plants of the new *Lantana* can be compared to plants of the cultivar Robpatcow, disclosed in U.S. Plant Pat. No. 12,450. In side-by-side comparisons conducted in Hawthorne, Fla., plants of the new *Lantana* differed from plants of the cultivar Robpatcow in the following characteristics:

1. Plants of the new *Lantana* were taller than plants of the cultivar Robpatcow.
2. Plants of the new *Lantana* flowered earlier than plants of the cultivar Robpatcow.
3. Plants of the new *Lantana* were more freely flowering than plants of the cultivar Robpatcow.

4. Plants of the new *Lantana* had golden yellow, orange and light red-colored flowers whereas plants of the cultivar Robpatcow had yellow orange and orange-colored flowers.
5. Plants of the new *Lantana* were more resistant to *Botrytis* than plants of the cultivar Robpatcow.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Lantana*. The photograph comprises a side perspective view of a typical flowering plant of 'LAX 600' grown in a container.

DETAILED BOTANICAL DESCRIPTION

In the following description, color references are made to The Royal Horticultural Society Colour Chart, 1995 Edition, except where general terms of ordinary dictionary significance are used. Plants used for the photographs and description were planted in 12.5-cm containers after rooting and grown for about six weeks during the spring in an outdoor nursery in Hawthorne, Fla. During the production of the plants, day temperatures ranged from 24° C. to 29° C. and night temperatures ranged from 18° C. to 21° C.

Botanical classification: *Lantana camara* cultivar LAX 600.

Parentage:

*Female parent.*—*Lantana camara* cultivar Tangerine, not patented.

*Male parent.*—Unidentified *Lantana camara* selection, not patented.

Propagation:

*Type cutting.*—Terminal cuttings.

*Time to initiate roots.*—About two weeks at 24° C.

*Time to develop roots.*—About four weeks at 24° C.

*Root description.*—Fine, fibrous; white in color.

*Rooting habit.*—Freely branching; dense.

Plant description:

*Form.*—Flowering subshrub; compact, upright and somewhat outwardly spreading; mounded. Freely branching; typically about two lateral branches potentially forming at every node; pinching enhances lateral branch development. Moderately vigorous growth habit.

*Plant height.*—About 15 cm.

*Plant diameter.*—About 21 cm.

*Lateral branches.*—Length: About 4.3 cm. Diameter: About 3 mm. Internode length: About 3 cm. Strength: Strong, but flexible. Texture: Rough, coarse pubescence. Color, young: Close to 144A. Color, mature: Close to 199A.

*Foliage description.*—Arrangement: Opposite; simple. Length: About 2.9 cm. Width: About 2.4 cm. Shape: Ovate. Apex: Acute. Base: Obtuse. Margin: Serrate. Texture, both surfaces: Leathery, rough, coarse; pubescent. Venation pattern: Pinnate, arcuate. Color: Developing and fully expanded foliage, upper surface: Darker green than 147A. Developing and fully expanded foliage, lower surface: More green than 147B. Venation, upper surface: Close to 147A. Venation, lower surface: Close to 147C. Petiole length: About 6 mm. Petiole diameter: About 2 mm. Petiole texture, upper and lower surfaces: Pubescent. Petiole color, upper surface: Close to 144A. Petiole color, lower surface: Close to 144B.

Flower description:

*Flower type and habit.*—Small salverform flowers arranged in axillary umbels; flowers face mostly upward or outwardly. Flowers self-cleaning. Very freely flowering with one to two inflorescences per node; typically about 22 to 24 flowers per umbel.

*Natural flowering season.*—Spring until frost in the autumn; flowering continuous during the flowering period.

*Flower longevity on the plant.*—About one week.

*Fragrance.*—Not detected.

*Inflorescence diameter.*—About 1.5 cm.

*Inflorescence height.*—About 3.5 cm.

*Flowers.*—Appearance: Flared trumpet, corolla fused; flowers roughly rectangular in shape. Diameter: About 7 mm by 8 mm. Height (depth): About 1.8 cm.

*Flower buds.*—Length: About 6 mm. Diameter: About 4 mm. Shape: Roughly ovoid. Color: Close to 144A.

*Corolla.*—Arrangement/appearance: Single whorl of four petals, fused into flared trumpet. Petal lobe length: About 3.5 mm. Petal lobe width: About 4 mm to 5 mm. Petal shape: Roughly spatulate to orbicular. Petal apex: Mostly rounded. Petal margin: Entire. Petal texture, upper and lower surfaces: Smooth, glabrous; satiny. Color: Petals, when opening, upper surface: Close to 17A, then overlain with close to 45A. Petals, when opening, lower surface: Close to 14A. Petals, fully opened, upper surface: Close to 45A; with development, color becoming closer to 53A. Petals, fully opened, lower surface: Close to 45B to 45C. Throat: Close to 15A to 17A. Tube: Close to 151A; towards the petal lobes, overlain with close to 45A.

*Calyx.*—Arrangement/appearance: One single calyx tube per flower. Sepal length: About 8 mm. Sepal width: About 2.5 mm. Sepal shape: Lanceolate with acute to acuminate apex and entire margin. Sepal texture, upper and lower surfaces: Pubescent. Sepal color, upper surface: 144A. Sepal color, lower surface: 144A to 146A.

*Peduncles.*—Length: About 2.75 cm. Diameter: About 1 mm. Angle: Mostly upright. Strength: Flexible, but strong. Texture: Pubescent. Color: Close to 144A.

*Pedicels.*—Length: Less than 1 mm. Diameter: Less than 1 mm. Angle: Upright. Strength: Flexible, but strong. Texture: Pubescent. Color: Close to 144A.

*Reproductive organs.*—Stamens: Quantity/arrangement: Four per flower, adnate to floral tube. Filament color: White, close to 155D. Anther shape: Oblong. Anther length: About 1.5 mm. Anther color: Close to 187A. Pistils: Quantity: One per flower. Pistil length: About 4 mm. Style length: About 2.5 mm. Style color: Close to 9A. Stigma shape: Rounded. Stigma color: Close to 9A. Ovary color: Brownish green. Fruit: Amount produced: Scarce. Diameter: About 5 mm. Shape: Roughly spherical. Texture: Smooth. Color: Close to 103A. Seed: Amount produced: Scarce. Diameter: About 2.5 mm. Color: Close to 200D.

Disease/pest resistance: Plants of the new *Lantana* have been observed to be relatively resistant to *Botrytis*. Plants of the new *Lantana* have not been observed to be resistant to pests and other pathogens common to *Lantana*.

Weather tolerance: Plants of the new *Lantana* have been observed to be very tolerant to rain and wind.

Temperature tolerance: Plants of the new *Lantana* have been observed to be tolerant to temperatures ranging from −6° C. to 38° C.

It is claimed:

1. A new and distinct cultivar of *Lantana* plant named 'LAX 600', as illustrated and described.

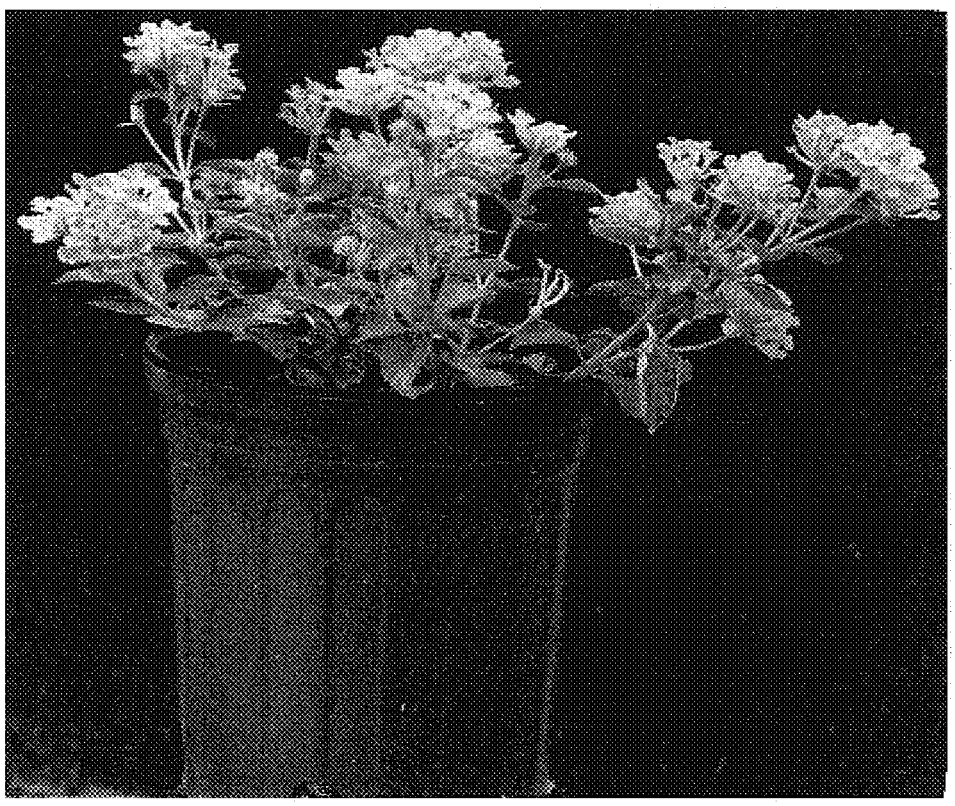

* * * * *